US010407497B2

(12) United States Patent
Raessler et al.

(10) Patent No.: US 10,407,497 B2
(45) Date of Patent: Sep. 10, 2019

(54) STUFFING BOX LOOSENING DEVICE AND METHOD

(71) Applicant: MCCANN EQUIPMENT LTD., Dorval (CA)

(72) Inventors: David Raessler, Edmonton (CA); Cameron Richard Green, St. Albert (CA)

(73) Assignee: MCCANN EQUIPMENT LTD., Dorval, Quebec (CA)

(*) Notice: Subject to any disclaimer, the term of this patent is extended or adjusted under 35 U.S.C. 154(b) by 80 days.

(21) Appl. No.: 15/524,031

(22) PCT Filed: Nov. 5, 2015

(86) PCT No.: PCT/CA2015/051142
§ 371 (c)(1),
(2) Date: May 3, 2017

(87) PCT Pub. No.: WO2016/074074
PCT Pub. Date: May 19, 2016

(65) Prior Publication Data
US 2017/0335638 A1  Nov. 23, 2017

Related U.S. Application Data

(60) Provisional application No. 62/078,206, filed on Nov. 11, 2014.

(51) Int. Cl.
*E21B 19/16* (2006.01)
*C07K 16/18* (2006.01)
(Continued)

(52) U.S. Cl.
CPC ........ *C07K 16/18* (2013.01); *A61K 39/39533* (2013.01); *A61K 45/06* (2013.01);
(Continued)

(58) Field of Classification Search
CPC ...... E21B 19/16; E21B 19/161; E21B 19/163; E21B 19/18; B25B 21/00; B25B 21/007
See application file for complete search history.

(56) References Cited

U.S. PATENT DOCUMENTS 3,041,901 A * 7/1962 Knights ................ E21B 19/163
81/57.2
4,442,892 A * 4/1984 Delesandri ............. E21B 19/00
137/315.02
(Continued)

FOREIGN PATENT DOCUMENTS

GB      2063746A A    6/1981

OTHER PUBLICATIONS

International Search Report of PCT/CA2015/051142 dated Jan. 18, 2016.
Written Opinion dated Jan. 18, 2016.

*Primary Examiner* — Kenneth L Thompson
(74) *Attorney, Agent, or Firm* — Norton Rose Fulbright Canada LLP

(57) ABSTRACT

A stuffing box loosening device for loosening a locking collar securing a stuffing box to a well head. The device includes a rotatable clamping tool having a clamp securable to an external surface of the locking collar. The clamp prevents relative rotational movement between itself and the locking collar. A force-receiving body extends away from the clamp. A main frame has a mounting portion securable to the well head, and the mounting portion prevents relative rotational movement between the main frame and the well head. A force-supporting body is attached to the mounting portion. An actuator is mounted to the force-supporting body and in operation extends to displace a second end to engage the force-receiving body of the clamping tool and apply a force thereto. The force rotates the clamp to loosen the locking collar.

19 Claims, 7 Drawing Sheets

(51) Int. Cl.
    *C07K 16/28*     (2006.01)
    *B23P 19/06*     (2006.01)
    *A61K 39/395*     (2006.01)
    *A61K 45/06*     (2006.01)
    *A61K 39/00*     (2006.01)
    *E21B 33/08*     (2006.01)

(52) U.S. Cl.
    CPC ............ B23P 19/061 (2013.01); C07K 16/28 (2013.01); E21B 19/16 (2013.01); *A61K 2039/505* (2013.01); *C07K 2317/24* (2013.01); *C07K 2317/56* (2013.01); *E21B 33/08* (2013.01)

(56) References Cited

U.S. PATENT DOCUMENTS

| | | | |
|---|---|---|---|
| 4,843,945 A | 7/1989 | Dinsdale | |
| 5,010,635 A | 4/1991 | Clark | |
| 5,060,542 A | 10/1991 | Hauk | |
| 7,146,880 B1 | 12/2006 | Francis et al. | |
| 8,413,728 B2 * | 4/2013 | Ledbetter | E21B 19/167 166/377 |
| 9,546,526 B2 * | 1/2017 | Li | E21B 19/163 |
| 9,782,876 B2 * | 10/2017 | Francis | B25B 21/005 |
| 2002/0157823 A1 | 10/2002 | Pietras et al. | |
| 2008/0307932 A1 | 12/2008 | Lauzon et al. | |
| 2014/0096651 A1 * | 4/2014 | Taggart | E21B 19/163 81/57.34 |

* cited by examiner

STUFFING BOX LOOSENING DEVICE AND METHOD

CROSS-REFERENCE TO RELATED APPLICATIONS

This application is a 371 of International Patent Application No. PCT/CA2015/051142 filed Nov. 5, 2015, which claims priority on U.S. Provisional Patent Application No. 62/078,206 filed Nov. 11, 2014, the entire contents of all of which are incorporated herein by reference.

TECHNICAL FIELD

The application relates generally to flow control devices for oil and gas wells and, more particularly, to removing stuffing boxes for replacement or repair.

BACKGROUND

Collars, nuts, or other locking mechanisms are used to secure one object to another. In the oil and gas industry, for example, a stuffing box is threaded into a flange of a well head and is secured to the well head with a threaded locking collar. With time, exposure, and wear, the locking collar degrades and becomes permanently attached to the flange of the well head and the stuffing box such that the locking collar cannot be easily removed. It then becomes very difficult to remove the stuffing box from the well head.

One technique for removing the locking collar involves using a sufficiently long pipe wrench and manually applying torque to the locking collar. It is very difficult, if not impossible, for one or more individuals to generate sufficient torque to loosen the locking collar. Using such a pipe wrench also poses safety issues. Furthermore, the space around many well heads is insufficient to use a sufficiently long pipe wrench.

Another technique for removing the locking collar calls for the assistance of a separate bolting crew, which will come and remove the well head itself, or some part thereof. The bolting crew will then take the well head offsite where it can employ specialised tools to attempt to unlock the locking collar so as to remove the stuffing box. Such a technique necessarily involves significant down time during which the well head is not productive, which represents an important additional expense.

SUMMARY

In one aspect, there is provided a stuffing box loosening device for loosening a locking collar securing a stuffing box to a well head, comprising: a rotatable clamping tool having a clamp securable to an external surface of the locking collar, the clamp preventing relative rotational movement between itself and the locking collar upon being secured thereto, and a force-receiving body extending away from the clamp and connected thereto; a main frame having a mounting portion securable to the well head, the mounting portion preventing relative rotational movement between the main frame and the well head upon being secured thereto, and a force-supporting body attached to the mounting portion; and an actuator having a first end removably mounted to the force-supporting body of the main frame and an opposed second end, the actuator in operation extending to displace the second end to engage the force-receiving body of the clamping tool and apply a force thereto, the force rotating the clamp to loosen the locking collar.

In another aspect, there is provided a method of loosening a locking collar securing a stuffing box to a well head, comprising: securing a clamp to an external surface of the locking collar to prevent relative rotational movement therebetween; securing a main frame to the well head to prevent relative rotational movement therebetween; and exerting a loosening force between the main frame and the clamp to rotate the clamp and loosen the locking collar.

In a further aspect, there is provided a stuffing box loosening device for loosening a locking collar securing a stuffing box to a well head, comprising: a rotatable clamping tool having a clamp securable to an external surface of the locking collar, the clamp preventing relative rotational movement between itself and the locking collar upon being secured thereto, and a force-receiving body extending away from the clamp and connected thereto; a main frame having a mounting portion securable to the well head, the mounting portion preventing relative rotational movement between the main frame and the well head upon being secured thereto, and a force-supporting body attached to the mounting portion and having first and second support plates interconnected by at least one connector plate, at least one of the first and second support plates having at least one groove therein; and an actuator having a first end removably mounted to the force-supporting body of the main frame and an opposed second end, the actuator in operation extending to displace the second end to engage the force-receiving body of the clamping tool and apply a force thereto, the force rotating the clamp to loosen the locking collar, the second end of the actuator having a rod pin engageable with the at least one groove.

In yet a further aspect, there is provided a stuffing box loosening device for loosening a locking collar securing a stuffing box to a well head, comprising: a rotatable clamping tool having a clamp securable to an external surface of the locking collar, the clamp preventing relative rotational movement between itself and the locking collar upon being secured thereto, and a force-receiving body extending away from the clamp and connected thereto; a main frame having a mounting portion with a first plate having a first collar located at a distal end of the first plate and securable to the well head, the mounting portion preventing relative rotational movement between the main frame and the well head upon being secured thereto, and a force-supporting body attached to the mounting portion, the distal end of the first plate having a plurality of bolt-head apertures therein, each bolt-head aperture mountable about a bolt head of a flange of the well head; and an actuator having a first end removably mounted to the force-supporting body of the main frame and an opposed second end, the actuator in operation extending to displace the second end to engage the force-receiving body of the clamping tool and apply a force thereto, the force rotating the clamp to loosen the locking collar.

In yet a further aspect, there is provided a stuffing box loosening device for loosening a locking collar securing a stuffing box to a well head, comprising: a rotatable clamping tool having a clamp securable to an external surface of the locking collar, the clamp preventing relative rotational movement between itself and the locking collar upon being secured thereto, and a force-receiving body extending away from the clamp and connected thereto; a main frame having a mounting portion securable to the well head, the mounting portion preventing relative rotational movement between the main frame and the well head upon being secured thereto, and a force-supporting body attached to the mounting portion, the force-supporting body having a rod aperture for receiving therein a barrel pin, the barrel pin being rotatable within the rod aperture; and an actuator having a first end removably mounted to the force-supporting body of the main frame and an opposed second end, the actuator in operation extending to displace the second end to engage the force-receiving body of the clamping tool and apply a force thereto, the force rotating the clamp to loosen the locking collar.

DESCRIPTION OF THE DRAWINGS

Reference is now made to the accompanying figures in which.

DETAILED DESCRIPTION

Figure 1:
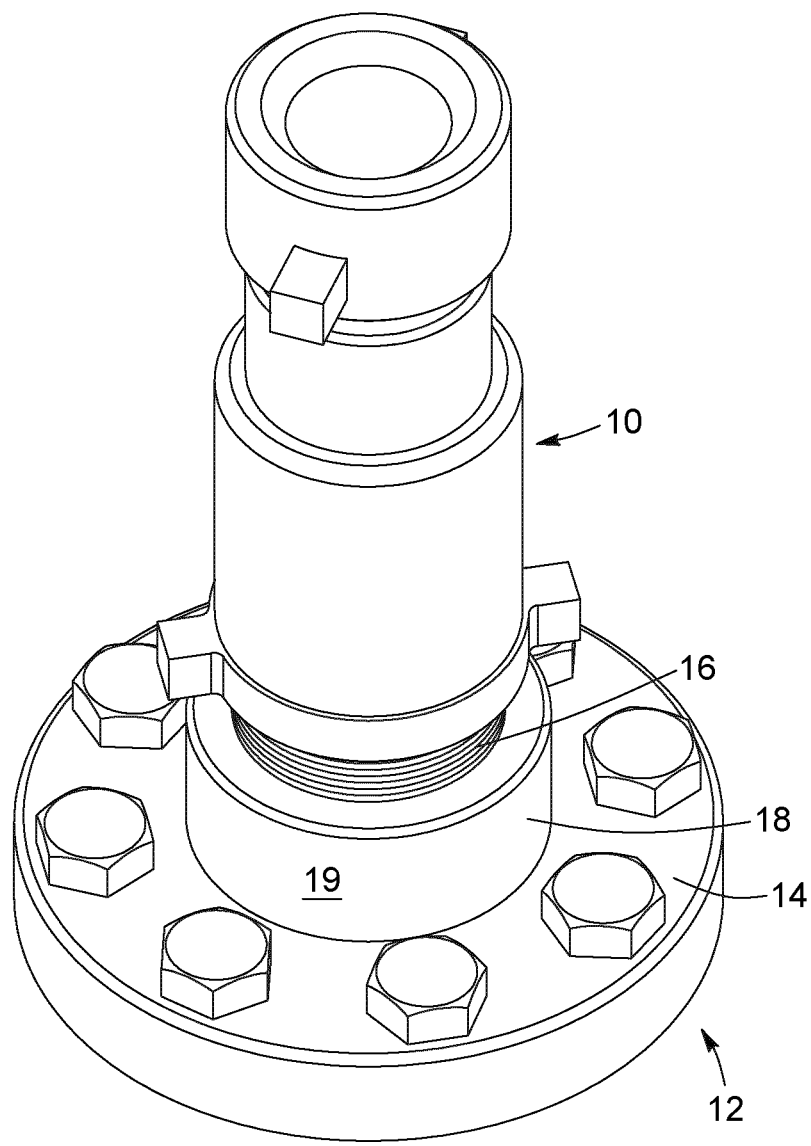
FIG. 1 is a perspective view of a stuffing box connected to a well head.

FIG. 1 illustrates a stuffing box 10 of the type used in the oil and gas industry mounted to a stationary well head 12, and more particularly, to the flange 14 of the well head 12. The stuffing box 10, which is a type of elongated body, can be of any given length and shape, and is therefore not limited to being cylindrical as shown in FIG. 1. The stuffing box 10 is a device that prevents leakage when a piston, rod, propeller shaft, or other moving part passes through a hole, such as through the output hole of the well head 12 at an oil and gas extraction facility. The stuffing box 10 is generally a hollow cylinder which has an internal box, or chamber, and generally contains a gland having compressed packing.

In well heads 12 where oil is lifted by means of a sucker rod pump, the rod operates by descending and ascending through the stuffing box 10. The passage of the rod through the stuffing box 10 prevents or minimises the escape of the pumped oil and diverts it into a side outlet for further processing or treatment.

The stuffing box 10 is mounted to the well head 12 by being threaded into a receiving portion of the flange 14 of the well head 12, the components here being shown having a generally upright orientation, although other orientations (i.e. horizontal, inclined from the vertical, etc.) are also possible. The threaded connection between the stuffing box 10 and the flange 14 can be further secured with a rotatable member. The rotatable member can be any collar, nut, coupler, or other similar device which rotates about an external surface 16 of the stuffing box 10 and/or the receiving portion of the flange 14 to secure the stuffing box 10 to the well head 12. In the present disclosure, the rotatable member is shown as a locking collar 18, but it will be appreciated that it can be any other suitable device. Such a locking collar 18 can be rotated along a threaded external surface 16 of the stuffing box 10 and/or the threaded exterior of the receiving portion of the flange 14, thereby securing the stuffing box 10 to the well head 12.

The shape of the collar 18 will generally depend on the shape of the outer surfaces to which is mounted. For example, where both the external surface 16 of the stuffing box 10 and the receiving portion of the flange 14 are cylindrical, the collar 18 can be a cylinder having an internal thread, or a polygonal locknut having a cylindrical inner aperture with an internal thread. Irrespective of its shape, it is known that over time the collar 18 can become difficult to remove from these outer surfaces because of wear, exposure to the elements, and exposure to the relatively harsh environment of an oil and gas well head 12. For example, when an external surface 19 of the collar 18 becomes rusted, worn, or otherwise degraded after a given period of time, it can be difficult to grip the external surface 19 with a conventional torque-applying tool. When this occurs, the collar 18 becomes very difficult, if not impossible, to remove with conventional tools. There is thus a need for a device which can loosen and/or remove the collar 18 when it has degraded to such a state.

Figure 2:
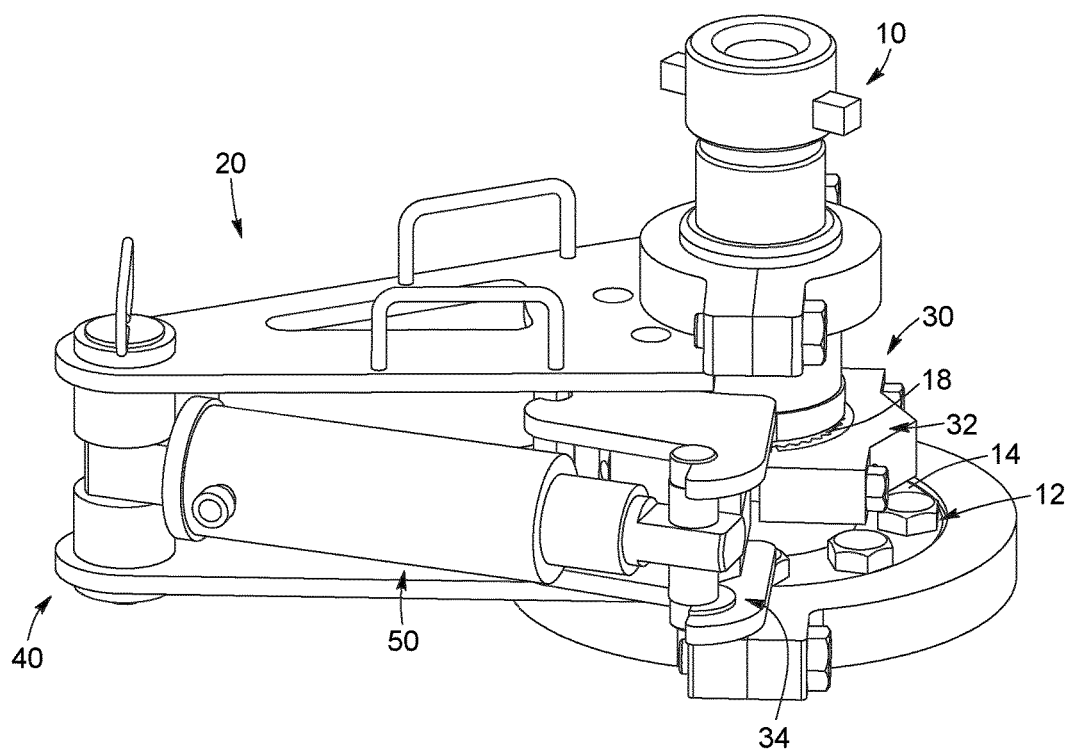
FIG. 2 is a perspective view of a stuffing box loosening device, according to an embodiment of the present disclosure, mounted to the well head and stuffing box of FIG. 1.

FIG. 2 illustrates an embodiment of such a stuffing box loosening device 20 (or simply "device 20"), which can be mounted and secured to an elongated body, such as the stuffing box 10 and well head 12, so that it can apply a torque to the rotatable degraded collar 18. In so doing, the device 20 helps to loosen, or "crack", the collar 18, thereby allowing the stuffing box 10 to be removed from the flange 14 of the well head 12.

The stuffing box loosening device 20 has a rotatable clamping tool 30 which is secured to the collar 18, a main frame 40 which is secured to the well head 12 and/or flange 14, and an actuator 50 which applies a force to the clamping tool 30.

The clamping tool 30 is secured to the external surface 19 of the collar 18 and receives a force from the actuator 50 in order to apply a loosening torque to the collar 18. The application of the torque to the collar 18 loosens its grip on the external surface 11 of the stuffing box 10 and/or on the receiving portion of the flange 14, thereby allowing the stuffing box 10 to be removed from the flange 14. The clamping tool 30 has a clamp 32 and a force-receiving body 34, both of which are now described.

The clamp 32 is securable to some, or all, of the external surface 19 of the collar 18. More particularly, the clamp 32 engages the external surface 19 such that substantially all the relative rotational movement between the collar 18 and the clamp 32 is prevented. Stated differently, when the clamp 32 is fixedly secured to the external surface 19 of the collar 18, there is substantially no slip between the clamp 32 and the collar 18. This allows the rotation of the clamp 32 to cause the collar 18 to also rotate. The clamp 32 can therefore be any collar, bracket, or other mechanical device which can bind, constrict, or press two or more parts together (i.e. press the clamp 32 against the external surface 19 of the collar 18).

Figure 3:
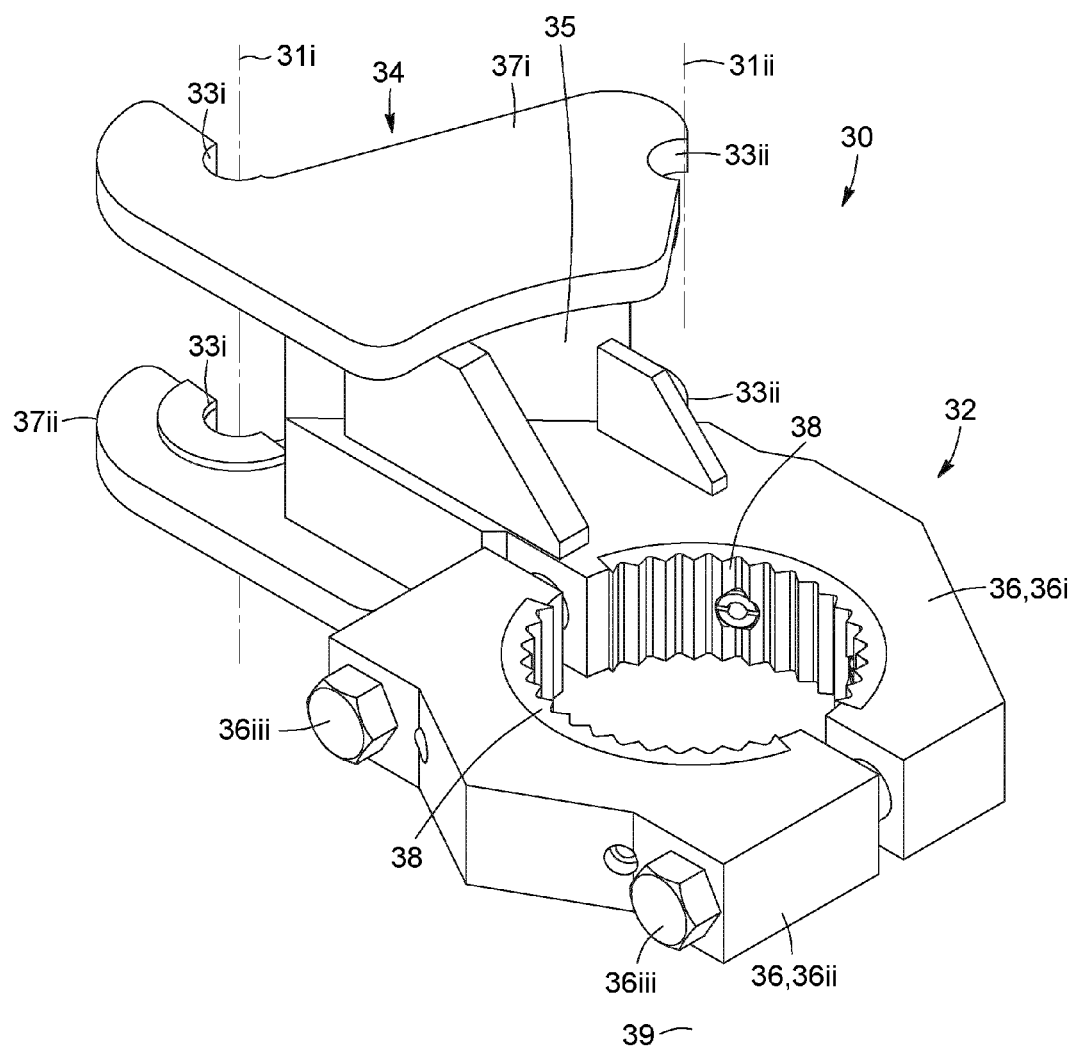
FIG. 3 is a perspective view of a clamping tool of the stuffing box loosening device of FIG. 2.

Referring to FIG. 3, the clamp 32 has two jaws/jaw plates 36, each one of which has a teeth set 38 which can be attached to the jaw plate 36, or integral therewith. A first one of the jaw plates 36i is integral with the force-receiving body 34, while a second one of the jaw plates 36i is a separate piece which can be mounted to the first jaw plate 36i via bolts 36*iii*. In operation, the first jaw set 36*i* is engaged against the external surface of the collar, and the second jaw set 36*ii* is aligned with the first jaw set 36*i* and bolted thereto. As the bolts 36*iii* are tightened, the teeth set 38 of each jaw exerts progressively increasing force against the external surface of the collar, thereby fixedly securing the clamp 32 to the collar. The orientation and disposition of the teeth sets 38 can vary. For example, the pitch and depth of the teeth on each teeth set 38 can be oriented in a direction to facilitate the loosening of the collar.

The force-receiving body 34 is attached to the clamp 32 or integral therewith, and is offset from the clamp 32 by extending away from the clamp 32. The offset force-receiving body 34 therefore defines a moment arm for the clamp 32, which increases the torque applied by the clamp 32 to the collar. More particularly, the force-receiving body 34 is offset from a center or central axis of rotation 39 of the clamp 32. In some embodiments, the force-receiving body 34 extends away from the clamp 32 along a direction being substantially perpendicular to the axis of rotation 39 of the clamp 32. Such a configuration of the force-receiving body 34 helps to reduce the shear or other undesirable force vectors acting against the clamp 32. When the force-receiving body 34 receives a force from the actuator, the clamp 32 is engaged by the force and applies a torque to the collar, thereby rotating the collar to loosen its grip about the external surface of the stuffing box. The force-receiving body 34 can therefore be any object which provides a moment arm against which the force from the actuator can be applied and transferred to the clamp 32.

The force-receiving body 34 can include first and second support plates 37*i*,37*ii*. The two support plates 37*i*,37*ii* are connected together via one or more connector plates 35. Such a framework provides support to the force-receiving body 34, and helps it to transfer the force received from the actuator to the clamp 32. In the embodiment of FIG. 3, the force-receiving body 34 has one or more grooves 33 which can receive therein a rod or other elongated object from the actuator (see FIG. 2).

More particularly, each of the first and second support plates 37*i*,37*ii* may have a first groove 33*i*. The first grooves 33*i* of the first and second support plates 37*i*,38*ii* are aligned along a first common axis 31*i*. Similarly, each of the first and second support plates 37*i*,37*ii* may have a second groove 33*ii*. The second grooves 33*ii* are also aligned along a second common axis 31*ii*. The aligned first and second grooves 33*i*,33*ii* each provide a grooved alignment into which an elongated object from the actuator, such as a rod pin which can engage a second end of the actuator, can be inserted. This allows the actuator to apply force to both the first and second support plates 37*i*,37*ii* simultaneously. The actuator exerts its force with the rod pin, which distributes the load to the support plates 37*i*,37*ii*, and then to the clamp 32.

Figure 4:
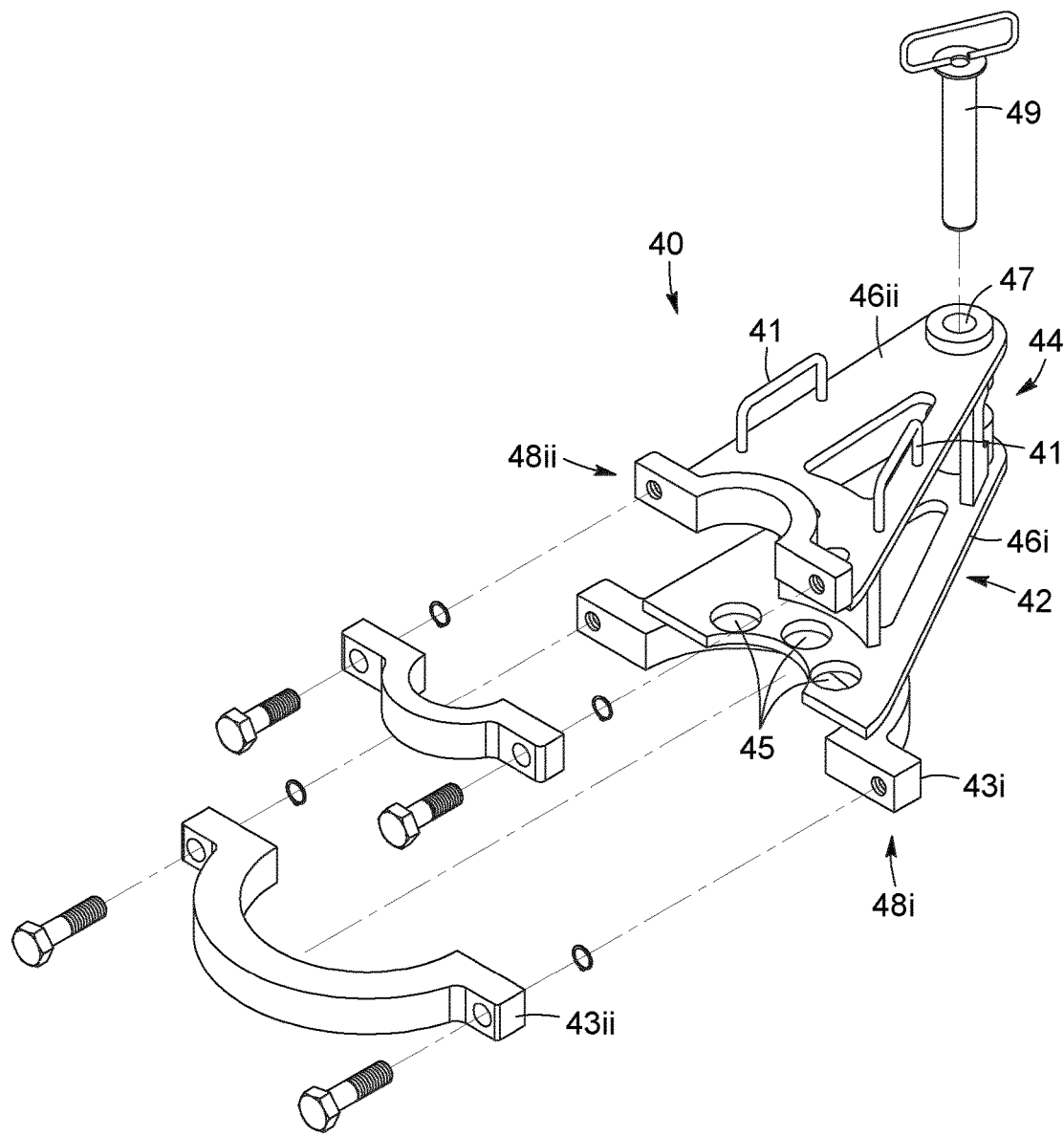
FIG. 4 is a perspective view of a main frame of the stuffing box loosening device of FIG. 2.

Referring now to FIG. 4, the main frame 40 forms the corpus of the device and provides structure thereto. It is secured to at least the well head and/or its flange such that it does not move relative thereto. In so doing, the main frame 40 provides a stable platform from which the actuator can exert force against the clamping tool. It will be appreciated that the main frame 40 can take may different shapes and configurations in order to achieve such functionality, some of which are described herein. The main frame 40 has a mounting portion 42 which is secured to at least the well head, and a force-supporting body 44 which houses and/or supports the actuator.

The mounting portion 42 engages at least the well head and/or its flange such that it substantially prevents relative rotational movement between the main frame 40 and the well head. In so doing, the mounting portion 42 secures the main frame 40 to the well head and allows force to be applied from the main frame 40 toward the clamping tool.

In the embodiment of FIG. 4, the mounting portion 42 has a first plate 46*i* having a distal first mounting collar 48*i* located at a distal extremity of the first plate 46*i*. The first plate 46*i* provides support to the main frame 40 against the forces exerted by the actuator. One embodiment of the first collar 48*i* is shown in FIG. 4, and includes two halves. In operation, a first half 43*i* of the first collar 48*i* is placed against the external surface of the well head flange. A second half 43*ii* of the first collar 48*i* is then placed against the external surface of the well head flange, and the ends of both halves 43*i*,43*ii* of the first collar 48*i* are aligned. Bolts are then inserted through the aligned ends. As the bolts are tightened, the first and second halves 43*i*,43*ii* of the mounting collar 48*i* exert progressively increasing force against the external surface of the well head flange, thereby fixedly securing the first plate 46*i*, and thus the main frame 40, to the well head. Other possible configurations for the mounting portion 42 possible, and it will therefore be appreciated that the shapes and configurations of the mounting portion 42 are not limited to those shown in FIG. 4.

The first plate 46*i* may include one or more bolt-head apertures 45 therein. The mounting portion 42, and thus the main frame 40, can be positioned in proper alignment with the well head and stuffing box by placing the bolt heads of the flange of the well head into the bolt-head apertures 45. It follows that the bolt-head apertures 45 can be circumferentially-spaced apart to match the anticipated location of the bolt heads of the flange. The engagement of each bolt head with the first plate 46*i* via the bolt-head apertures 45 also increases the ability of the first plate 46*i* to reduce and/or prevent the relative rotational movement between the main frame 40 and the well head which may occur as a reaction to the application of force against the clamping tool.

The mounting portion 42 may also include a second plate 46*ii* which is spaced apart from the first plate 46*i*, and connected thereto by one or more gussets. Each of the plates 46*i*,46*ii* can have apertures or cut-outs which lower the weight of the plates 46*i*,46*ii* without compromising the structural support they provide. The main frame 40 can also have one or more handles 41 which allow the main frame 40, and thus the device, to be portable and carried by one or more people.

The second plate 46*ii* can include different interfaces linking it to the stuffing box. One such interface is a second mounting collar 48*ii* which engages the external surface of the stuffing box. Similarly to the first collar 48*i*, the second collar 48*ii* can include two collar halves which are mechanical tightened about the external surface of the stuffing box with bolts, as described above. The engagement of the second collar 48*ii* with the stuffing box provides additional stability when mounting the device to the well head, such as by preventing the device from toppling over. In some instances, the second collar 48*ii* can be tightened about the external surface of the stuffing box so as to substantially prevent relative rotational movement between the stuffing box and the second collar 48*ii*. This configuration may be implemented, for example, where it is desired to focus substantially all of the loosening torque on only the collar.

The positioning of the second plate 46*ii* with respect to the clamp is dependent on numerous factors, such as the space available on the stuffing box and the force provided by the actuator, to name a few. In the embodiment of FIG. 4, the first collar 48i can be secured to the well head below the clamp, and the second collar 48ii can be mounted about the external surface of the stuffing box above the clamp.

The force-supporting body 44 is attached to the mounting portion 42. It provides a platform for receiving the actuator and for transferring the reactionary force from the actuator to the main frame 40. The force-supporting body 44 therefore assists the main frame 40 in providing a stable platform for applying force to the clamping tool. The force-supporting body 44 can have a base linked to the mounting portion 42 and against which an end of the actuator can be mounted. In the embodiment of FIG. 4, the force-supporting body 44 is defined by a rod aperture 47 in the second plate 46ii into which a barrel pin 49 can be removably inserted. The insertion of the barrel pin 49 into to the rod aperture 47 helps to secure a first end of the actuator to the main frame 40. When the device is in a vertical orientation, the barrel pin 49 supports a horizontally-inclined actuator. The first plate 46i can also have suitable structure to house and/or secure the barrel pin 49. The barrel pin 49 is rotatable within the rod aperture 47. This allows the first end of the actuator to also be rotatable, thereby allowing the force-application end of the actuator to be rotatably displaced. As is discussed in greater detail below, this helps to vary the application of force by the actuator against different portions of the clamping tool.

Figure 5A:
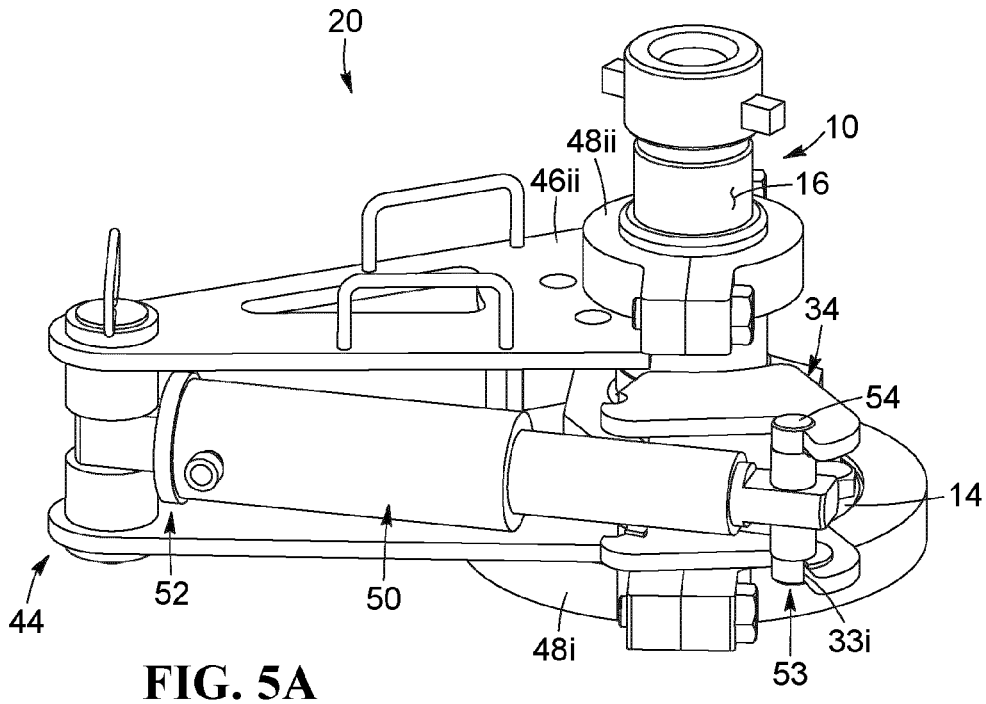
FIG. 5A is a perspective view of the loosening device of FIG. 2 mounted to the well head and stuffing box of FIG. 1, an actuator of the stuffing box loosening device being shown in a first extended position.
Figure 5B:
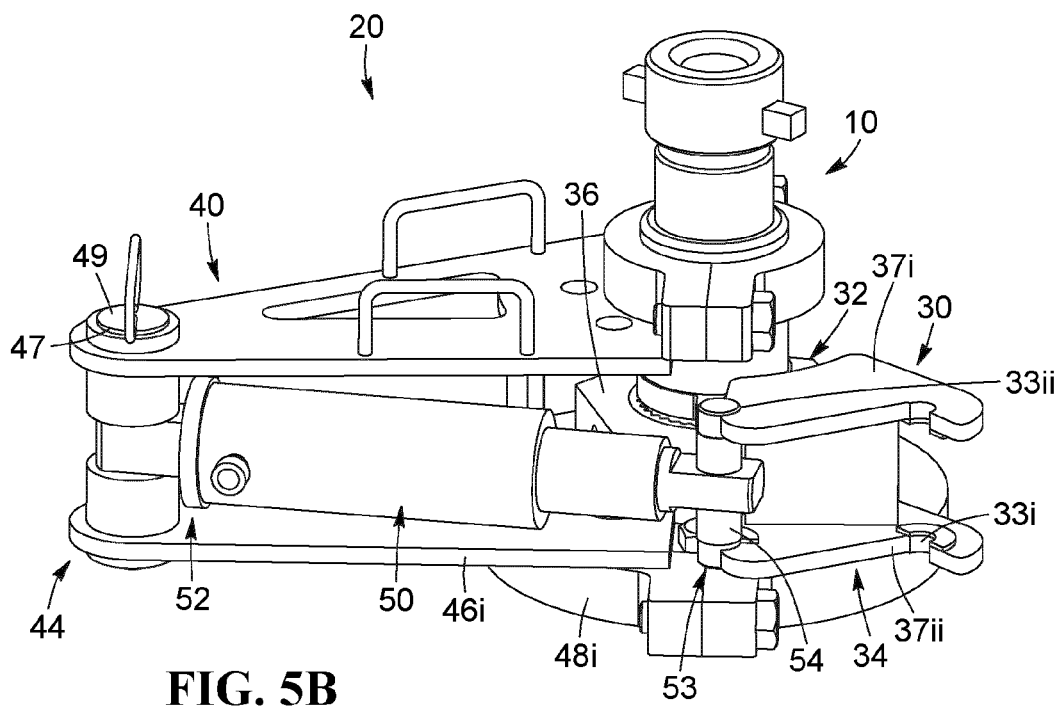
FIG. 5B is a perspective view of the loosening device of FIG. 2 mounted to the well head and stuffing box of FIG. 1, the actuator of the stuffing box loosening device being shown in a second extended position.

Referring to FIGS. 5A and 5B, the actuator 50 provides the force needed to loosen or "crack" the collar stuck on the stuffing box 10 and flange 14. The actuator 50 includes a linear actuator, and is typically a hydraulic actuator 50 supplied with hydraulic fluid from a feed line. The actuator 50 may be of a different type (e.g. mechanical, electrical, pneumatic, etc.) depending on the force desired, weight and volume requirements, and other possible factors. A first end 52 of the actuator is secured to the force-supporting body 44, while a second end 53 is typically a free end which protrudes away from the force-supporting body 44. In operation, the actuator 50 is activated and produces a linear force. This extends the second end 53 away from the force-supporting body 44 and towards the force-receiving body 34. The second end 53 eventually engages the force-receiving body 34, which in turns transfers the linear force into a rotational force (i.e. loosening torque) applied to the clamp 32, and applies the loosening torque to the collar. Other possible configurations for the actuator 50 are also within the scope of the present disclosure.

The installation of the device 20 and its operation will now be explained with reference to FIGS. 5A and 5B.

The clamp 32 is fixedly secured to the external surface of the collar to prevent relative rotational movement between the clamp 32 and the collar. To allow for adjusting the positioning of the clamp 32 later on, the bolts used for tightening the jaw sets 36 of the clamp 32 do not need to be fully tightened.

The main frame 40 is then mounted to the well head. The first plate 46i of the main frame 40 is mounted to the flange 14 of the well head. This can be achieved by placing the bolt-head apertures over the bolt heads of the flange 14. The first collar 48i of the first plate 46i is tightened about the flange 14 to prevent relative rotational movement between the main frame 40 and the well head. The position of the clamp 32 on the collar can now be adjusted so that the force-receiving body 34 aligns with the second end 53 of the actuator 50, the first end 52 of which may already be mounted to the force-supporting body 44. The bolts of the jaws 36 can then be tightened to secure the clamp 32 in place. If desired, the second plate 46ii of the main frame 40 and its second collar 48ii can be mounted about the external surface 16 of the stuffing box 10.

With the main frame 40 and the clamp 32 now in position, the loosening force can be applied with the second end 53 of the actuator 50. The actuator 50, mounted to the main frame 40 at the force-supporting body 44, extends the second end 53 to engage the force-receiving body 34. More particularly, in the embodiment shown in FIG. 5A, the free second end 53 has a rod pin 54 which aligns with and engages the first grooves 33i of the force-receiving body 34. A linear force is therefore applied to the force-receiving body 34, and as the second end 53 pushes the first grooves 33i, a rotational loosening torque is produced that acts on the clamp 32.

Once full extension of the second end 53 has occurred, and if desired, the free second end 53 of the actuator 50 can be repositioned by rotating with the barrel pin 49 in the rod aperture 47 until the rod pin 54 of the second end 53 engages the second grooves 33ii, as shown in FIG. 5B. The second end 53 and its rod pin 54 can again be extended, this time against the second grooves 33ii, to produce another loosening torque acting on the clamp 32 to rotate the clamp 32 a second rotational extent. It can thus be appreciated that this configuration of the first and second grooves 33i,33ii, where the first grooves 33i are located on the first and second support plates 37i,37ii forward of the second grooves 33ii in a direction of extension of the second end 53 of the actuator 50, allows multiple applications of the loosening torque without having to reposition the device 20. In an embodiment, the second grooves 33ii are located closer to the axis of rotation of the clamp 32, as measured along a line that is perpendicular to the axis of rotation, than the first grooves 33i. This reflects the reality that less loosening torque may be required when applying the loosening force against the second grooves 33ii because the collar may already have been "cracked".

It can thus be appreciated that the application of a linear force by the actuator 50 produces a loosening torque which acts on the clamp 32, and thus acts on the collar as well. The torque applied will eventually loosen, or "crack" the collar. Once so loosened, the positioning of the device 20 can be adjusted and it can be used again, or the device 20 can be removed from the well head and/or stuffing box 10 and another conventional tool can be used to further loosen and/or remove the collar. The stuffing box 10 can now be removed to be repaired or replaced.

Figure 6:
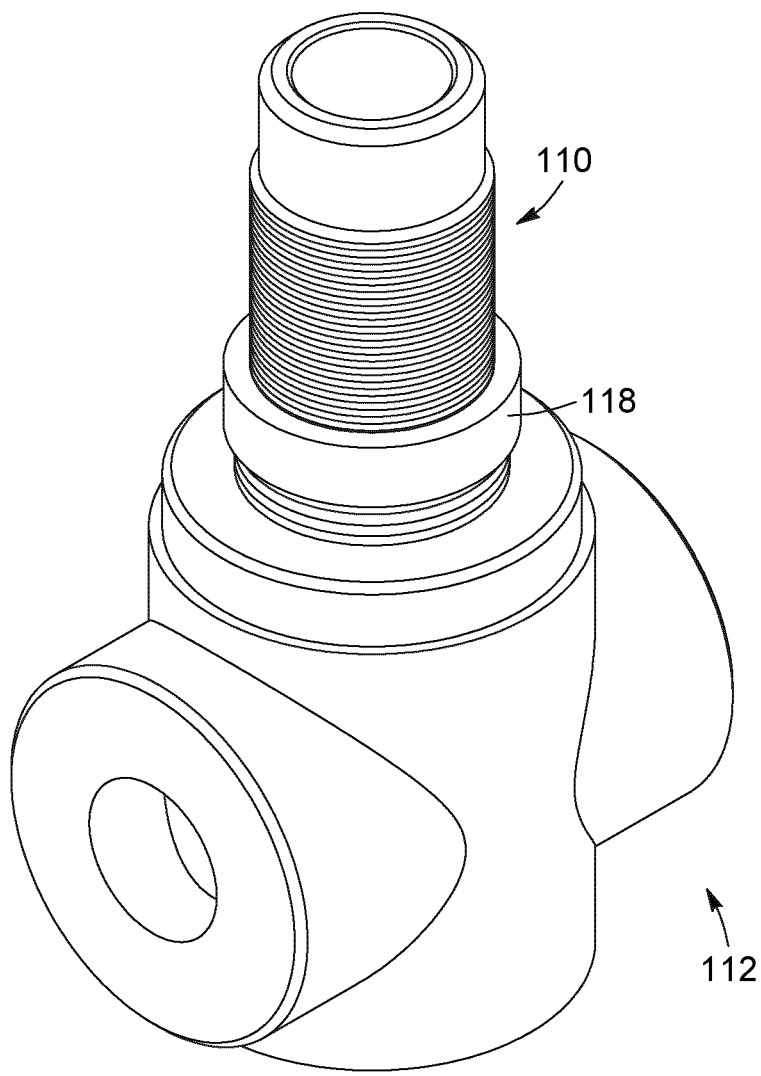
FIG. 6 is a perspective view of a stuffing box connected to a well head of the flow-cross body type.

FIG. 6 provides a schematic illustration of another type of oil and gas well head 112, which have "flow cross" bodies. Flow-cross body well heads 112 represent a significant portion of oil and gas well heads in certain geographic locations, and also include a stuffing box 110. Flow-cross body well heads 112 do not have a horizontal flange surface against which the device disclosed herein can rest. Therefore, the stuffing box 110 used with flow-cross boy well heads 112 is not mounted directly to a flange of the well head 112, as described above, and secured thereto with a locking collar 118. In order for the device disclosed herein to be used with a well head 112 which does not have a flange, an adapter can be provided to simulate the flange of a well head and allow the device 20 to be mounted thereto.

Figure 7A:
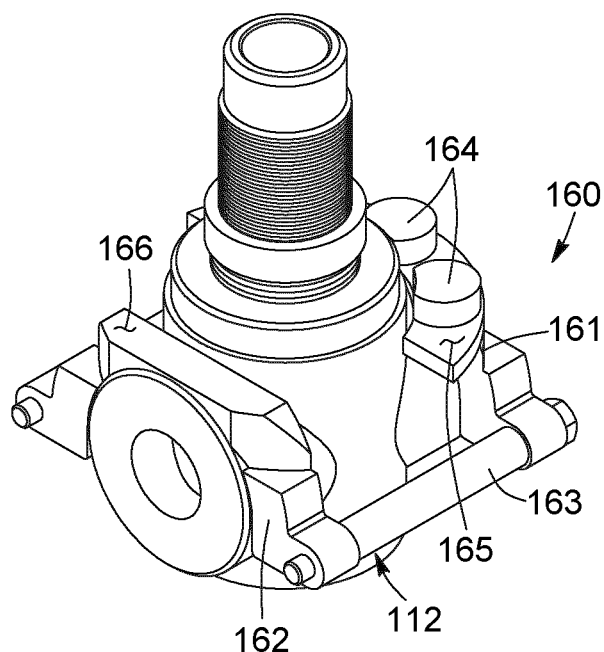
FIG. 7A is a perspective view of an adapter mounted to the well head of FIG. 6.
Figure 7B:
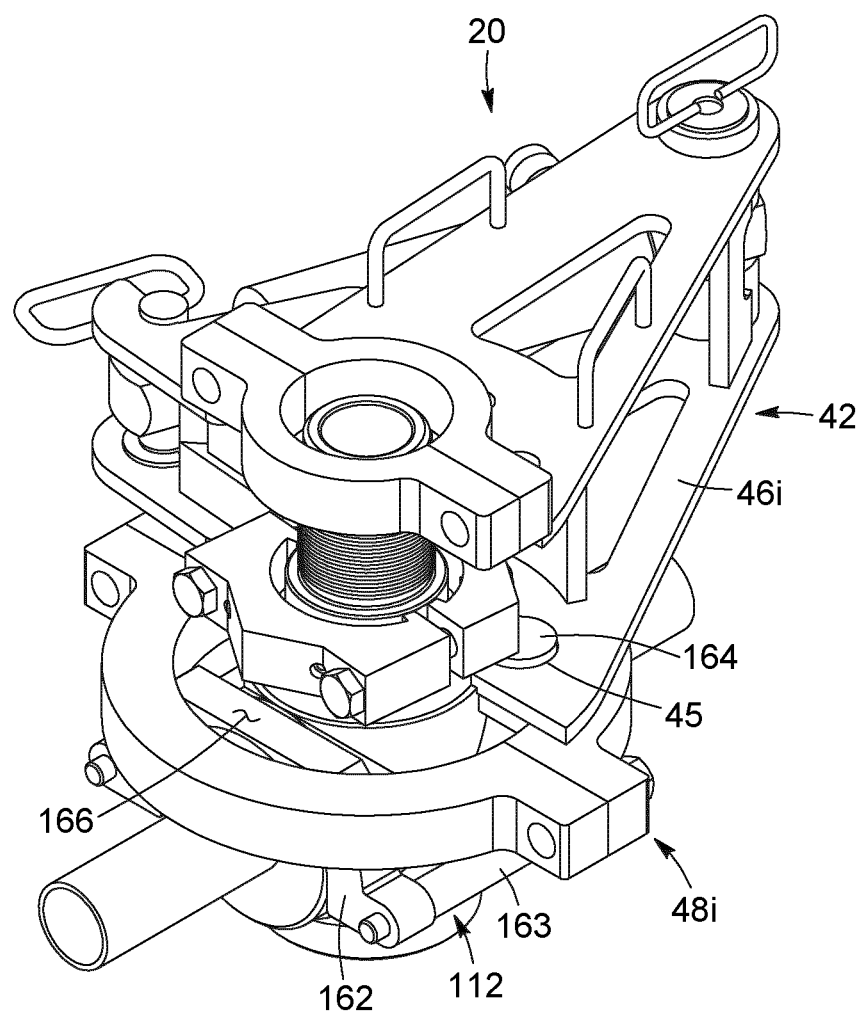
FIG. 7B is a perspective view of the stuffing box loosening device of FIG. 2 mounted to the adapter of FIG. 7A.

FIGS. 7A and 7B illustrate an adapter 160 which can be mounted to the flow-cross body well head 112. The adapter 160 can be used to mount the loosening device 20 to such a well head 112. The adapter 160 has a first curved base portion 161 and a second base portion 162. Both base portions 161,162 are joined together around the flow-cross body with threaded pipes 163 and bolts. Each of the base portions 161,162 mimics a flange used on conventional well heads and allows the device 20 to be used on less conventional well heads 112 which do not have flanges, such as those of the flow-cross body variety.

The first base portion 161 includes spaced-apart protrusions 164 extending from an exposed surface 165 of the first base portion 161. The protrusions 164 mimic the bolt heads projecting from the flange of a conventional well head, and are positioned, shaped, and sized to be received within the bolt-head apertures 45 of the first plate 46i of the device 20. The exposed surface 165 can also be curved in order to mimic a portion of the periphery of the conventional flange. The second base portion 162 has an exposed resting surface 166 which mimics the upper planar surface of the conventional flange, and is configured to engage at least a portion of the first collar 48i.

It can thus be appreciated that the adapter 160 allows the first plate 46i of the mounting portion 42 to be fixedly secured to the adapter 160, and thus, to the flow-cross body well head 112. The bolt-head apertures 45 of the first plate 46i are mounted about the protrusions 164 of the first base portion 161, while the first collar 48i engages the sides of the exposed resting surface 166. The two collar halves 43i,43ii are then secured together about the adapter 160 with bolts. The device 20 is therefore mounted to the flow-cross body well head 112 and is prevented from rotating relative thereto by the adapter 160. The device 20 can now be used as described above.

There is also disclosed a method of loosening a locking collar which secures a stuffing box to a well head. The method includes securing a clamp to an external surface of the locking collar to prevent relative rotational movement therebetween. The method also includes securing a main frame to the well head to prevent relative rotational movement therebetween. The method also includes applying a loosening force originating at the main frame and impacting the clamp to rotate the clamp and loosen the locking collar.

In light of the preceding, it can be appreciated that the loosening device 20 described herein can be quickly and easily mounted to, and removed from, a well head 12,112 and/or stuffing box 10,110 or other elongated body in order to remove a rotatable member (e.g. locking collar 18,118) fixed thereto. The device 20 therefore helps to minimise the unproductive down time of the well head 12,112, and further reduces any risk of injury associated with conventional loosening techniques.

The device 20 is compact and thus easily portable. The ability of a single actuator 50 to apply force from the main frame 40 to the clamping tool 30 in substantially the same horizontal or vertical plane allows the device 20 to remain relatively compact, and decrease its manufacturing costs by limiting the number of costly actuators needed to apply the loosening torque. This contrasts with some prior art devices, which require multiple actuators and multiple clamping devices to loosen one body with respect to another. The device 20 is also relatively lightweight and easily portable by one or two people because of the conveniently positioned handles 41. The device 20 can therefore be brought to any location with relative ease.

The device 20 disclosed herein can also be mounted to different types of well heads 12,112, such as those with and without flanges. Some of these well heads include Galaxy Flange Style well heads 12, and Guiberson flow-cross style well heads 112. The device 20 herein can therefore be considered to be a "stuffing box removal tool".

The above description is meant to be exemplary only, and one skilled in the art will recognize that changes may be made to the embodiments described without departing from the scope of the invention disclosed. For example, although the loosening device 20 is described herein as being used with oil and gas well heads, it will be appreciated that it can be used in other industries, and with other objects. Similarly, the loosening device 20 can be used with both vertically-inclined and horizontally-inclined elongated bodies. Still other modifications which fall within the scope of the present invention will be apparent to those skilled in the art, in light of a review of this disclosure, and such modifications are intended to fall within the appended claims.

The invention claimed is:

1. A stuffing box loosening device for loosening a locking collar securing a stuffing box to a well head, comprising:
   a rotatable clamping tool having a clamp with jaw plates, the jaw plates having teeth and being attachable together to engage the teeth with an external surface of the locking collar to secure the clamp thereto, the clamp preventing relative rotational movement between itself and the locking collar upon being secured thereto, and a force-receiving body extending away from the clamp and connected thereto;
   a main frame having a mounting portion securable to the well head, the mounting portion preventing relative rotational movement between the main frame and the well head upon being secured thereto, and a force-supporting body attached to the mounting portion; and
   an actuator having a first end removably mounted to the force-supporting body of the main frame and an opposed second end, the actuator in operation extending to displace the second end to engage the force-receiving body of the clamping tool and apply a force thereto, the force rotating the clamp to loosen the locking collar.

2. The loosening device of claim 1, wherein the force-receiving body extends away from the clamp along a direction being substantially perpendicular to an axis of rotation of the clamp.

3. The loosening device of claim 1, wherein the force-receiving body includes first and second support plates interconnected by at least one connector plate, at least one of the first and second support plates having at least one groove therein to receive the second end of the actuator.

4. The loosening device of claim 3, wherein each of the first and second support plates has a first groove therein, the first grooves of the first and second support plates being aligned along a first common axis.

5. The loosening device of claim 4, wherein each of the first and second support plates has a second groove therein, the second grooves of the first and second support plates being aligned along a second common axis.

6. The loosening device of claim 5, wherein the first grooves are located on the first and second support plates forward of the second grooves in a direction of extension of the actuator.

7. The loosening device of claim 4, wherein the second end of the actuator comprises a rod pin engageable with at least one of the first and second grooves.

8. The loosening device of claim 1, wherein the mounting portion includes a first plate having a first collar located at a distal end of the first plate and securable to the well head.

9. The loosening device of claim 8, wherein the distal end has a plurality of bolt-head apertures therein, each bolt-head aperture mountable about a bolt head of a flange of the well head.

10. The loosening device of claim 9, wherein the main frame includes an adapter mountable to the well head and approximating a well head flange, the first plate being securable to the adapter.

11. The loosening device of claim 10, wherein the adapter has a first curved base portion having spaced-apart protrusions extending from an exposed surface thereof, each protrusion being positioned, shaped, and sized to be received in a corresponding bolt-head aperture of the first plate.

12. The loosening device of claim 10, wherein the adapter has a second base portion having an exposed resting surface positioned, shaped, and sized to engage at least a portion of the first collar.

13. The loosening device of claim 8, wherein the mounting portion includes a second plate spaced-apart from and connected to the first plate and having a second collar mountable about an external surface of the stuffing box.

14. The loosening device of claim 13, wherein the first collar is securable to the well head below the clamp, and the second collar is mountable about the external surface of the stuffing box above the clamp.

15. The loosening device of claim 13, wherein the force-supporting body includes a rod aperture in the second plate and a barrel pin, the barrel pin being removably inserted through the rod aperture to secure the first end of the actuator to the main frame, the barrel pin being rotatable within the rod aperture.

16. A method of loosening a locking collar securing a stuffing box to a well head, comprising:

securing a clamp to an external surface of the locking collar to prevent relative rotational movement therebetween;

securing a main frame to the well head to prevent relative rotational movement therebetween; and exerting a loosening force between the main frame and the clamp to rotate the clamp and loosen the locking collar, including applying the loosening force to impact a first portion of the clamp to rotate the clamp a first rotational extent, and subsequently applying the loosening force to impact a second portion of the clamp spaced apart from the first portion to rotate the clamp a second rotational extent.

17. The method of claim 16, wherein exerting the loosening force includes rotating the clamp about an axis of rotation and impacting the clamp at a location thereon being spaced apart from the axis of rotation and substantially perpendicular thereto.

18. The method of claim 16, wherein exerting the loosening force includes pivoting application of the loosening force originating at the main frame to impact the clamp at different locations thereon.

19. The method of claim 16, wherein exerting the loosening force includes applying the loosening force originating at the main frame and impacting the clamp in a single horizontal plane.

* * * * *